(12) United States Patent
Stanjek et al.

(10) Patent No.: US 8,288,578 B2
(45) Date of Patent: Oct. 16, 2012

(54) PROCESS FOR PREPARING ISOCYANATOORGANOSILANES

(75) Inventors: Volker Stanjek, Ampfing (DE); Frank Baumann, Tittmoning (DE); Thomas Frey, Burghausen (DE)

(73) Assignee: Wacker Chemie AG, Munich (DE)

( * ) Notice: Subject to any disclaimer, the term of this patent is extended or adjusted under 35 U.S.C. 154(b) by 486 days.

(21) Appl. No.: 12/526,192

(22) PCT Filed: Jan. 25, 2008

(86) PCT No.: PCT/EP2008/050847
§ 371 (c)(1),
(2), (4) Date: Aug. 27, 2009

(87) PCT Pub. No.: WO2008/095791
PCT Pub. Date: Aug. 14, 2008

(65) Prior Publication Data
US 2010/0004475 A1    Jan. 7, 2010

(30) Foreign Application Priority Data
Feb. 7, 2007    (DE) .......................... 10 2007 006 147

(51) Int. Cl.
*C07F 7/20* (2006.01)
(52) U.S. Cl. ........................................ 556/414
(58) Field of Classification Search .................. None
See application file for complete search history.

(56) References Cited

U.S. PATENT DOCUMENTS

| | | | |
|---|---|---|---|
| 4,654,428 A | 3/1987 | Kurashima et al. | |
| 4,661,627 A | 4/1987 | Regelman | |
| 4,697,009 A | 9/1987 | Deschler et al. | |
| 4,735,979 A | 4/1988 | Beers et al. | |
| 6,008,396 A | 12/1999 | Sheridan et al. | |
| 2002/0016486 A1 | 2/2002 | Pinske | |
| 2004/0049064 A1 | 3/2004 | Kammel et al. | |
| 2004/0204539 A1 | 10/2004 | Schindler et al. | |
| 2006/0111505 A1 | 5/2006 | Schindler et al. | |
| 2007/0066784 A1 | 3/2007 | Radinger et al. | |
| 2007/0149797 A1 | 6/2007 | Rudinger et al. | |

FOREIGN PATENT DOCUMENTS

| | | |
|---|---|---|
| DE | 3544601 A1 | 6/1986 |
| DE | 10108543 C1 | 4/2002 |
| EP | 0212058 A2 | 3/1987 |
| EP | 0649850 A1 | 4/1995 |
| EP | 1010704 A2 | 6/2000 |
| EP | 1343793 B1 | 5/2004 |
| EP | 1421129 B1 | 6/2005 |
| JP | 63-500178 A | 1/1988 |
| JP | 63-51367 A | 3/1988 |
| JP | 9-143141 A | 6/1997 |
| JP | 2005-501146 A | 1/2005 |
| WO | 2004022618 A1 | 3/2004 |
| WO | 2005055974 A2 | 6/2005 |
| WO | 2005056564 A1 | 6/2005 |
| WO | 2005056565 A1 | 6/2005 |

OTHER PUBLICATIONS

Kunststoff Handbuch, 1984, pp. 71-72, translation of the 2nd paragraph on p. 72.*
Becker et al Kunststoff Handbuch, 1984, pp. 71-72, official translation of the 2nd paragraph on p. 72.*
Becker, G.W., Braun, D., "Kunststoff Handbuch", Munchen, Carl Hanser Verlag, DE, vol. 7, 1984, pp. 71-72.
The doctoral thesis, "Natuerliche Radionuklide in Grundwaessem des Kantons Graubuenden Dissertation von Otmar Deflorin," S. 59, 60, "Spuelen" und "Messung", 2004.
Data Sheet "Datenblatt Firma Linde bzgl. N2", 2010.

* cited by examiner

*Primary Examiner* — Yevegeny Valenrod
(74) *Attorney, Agent, or Firm* — Brooks Kushman P.C.

(57) ABSTRACT

The invention provides a process for preparing silanes which possess an isocyanate function, in which the silanes, after their chemical preparation, are purified and, after the purification, are handled exclusively in an atmosphere with a relative air humidity below 10%.

13 Claims, No Drawings

PROCESS FOR PREPARING ISOCYANATOORGANOSILANES

CROSS-REFERENCE TO RELATED APPLICATION

This application is the U.S. national phase of PCT Appln. No. PCT/EP2008/050847 filed Jan. 25, 2008 which claims priority to German application DE 10 2007 006 147.3 filed Feb. 7, 2007.

BACKGROUND OF THE INVENTION

1. Field of the Invention

The invention relates to a process for preparing silanes which have an isocyanate function, in which improved storage stability is achieved.

2. Description of the Related Art

There has for a long time been great interest in an economical method of preparing isocyanatoorganosilanes in high yields and purities. The compounds mentioned are of great economic importance.

Isocyanatosilanes can be used, for example, as bonding agents between organic polymers and inorganic materials. However, isocyanatoorganosilanes are used in industry first and foremost for the termination of organic polyols (e.g. polyether polyols, polyurethanes, polyesters or poly(meth)acrylates. The resulting alkoxysilane-terminated prepolymers cure on contact with atmospheric moisture and are used, inter alia, as adhesives and sealants or as surface coating resins or as constituents of surface coating resins.

In the prior art, use is usually made of conventional γ-isocyanatopropylsilanes of the formula (1)

$$OCN-(CH_2)_3-Si(OR')_x(R'')_{3-x} \quad (1),$$

where R' and R'' are alkyl radicals and x is 0-3, preferably 3 or 2.

However, there has recently been particular interest in the α-isocyanatomethylsilanes of the general formula (2)

$$OCN-CH_2-Si(OR')_x(R'')_{3-x} \quad (2),$$

where R' and R'' and x are as defined above.

These α-isocyanatomethylsilanes have a particularly high reactivity toward atmospheric moisture and are suitable for preparing alkoxysilane-terminated prepolymers having a high but regulatable curing rate (described, for example, in EP 1 421 129 and WO 2004/022618). In addition, the corresponding α-silane-terminated prepolymers can also be crosslinked without the tin catalysts which are of toxicological concern (described, inter alia, in EP 1 421 129).

Various processes for preparing isocyanatoorganosilanes are known. Thus, EP 0 212 058 describes a process in which silanes having a urea unit are thermally dissociated in the liquid phase to form isocyanatoorganosilanes and the corresponding amines or amides.

EP 1 010 704 discloses a process for preparing isocyanatoorganosilanes, in which carbamatoorganosilanes are thermally dissociated in the liquid phase in the presence of tin(II) chloride as catalyst to form the corresponding isocyanatoorganosilanes.

DE 101 08 543 describes the preparation of isocyanatoorganosilanes from the corresponding carbamatoorganosilanes and alkylchlorosilanes or vinylchlorosilanes.

Furthermore, U.S. Pat. No. 6,008,396 discloses a process in which carbamatoorganosilanes are converted in inert hot media with elimination of alcohol into the corresponding isocyanatosilanes which are then removed directly from the reaction mixture by distillation.

The thermal dissociation of carbamatoorganosilanes to form isocyanatoorganosilanes and methanol is also described in EP 0 649 850 where the dissociation takes place in the gas phase under atmospheric or reduced pressure. The reaction is preferably carried out in a tube reactor. An improvement in this process, in which the carbamate dissociation is carried out in the presence of a heterogeneous catalyst is also known from EP 1 343 793. If appropriate, the thermolysis can also be carried out using the microstructure apparatuses described in WO 2005/056565.

A further process in which the isocyanatoorganosilanes are prepared under the action of microwaves is described in WO 2005/056564. Finally, WO 2005/055974 describes this microwave process in combination with fluidizing solid particles.

The processes described in the prior art are usually used only for preparing the conventional γ-isocyanatopropylsilanes of the formula (1). However, they are, at least in principle, also suitable for preparing α-isocyanatomethylsilanes of the formula (2). Without exception, though, they have the disadvantage that the α-isocyanatomethylsilanes of the formula (2) obtained by all the processes are relatively unstable and, at least at room temperature, do not have a satisfactory storage stability. Thus, storage at room temperature for only a few weeks, sometimes even only a few days depending on the production process, is enough for decomposition of significant proportions (i.e. >>10%) of the respective α-isocyanatomethylsilane to be observed. It is also notable, in particular, that the decomposition of α-isocyanatomethylsilanes also takes place in sealed containers with exclusion of air. Here, the α-isocyanatomethylsilanes of the formula (2) differ significantly from conventional isocyanates without a silane unit since the latter can usually be stored without problems for months in airtight containers.

SUMMARY OF THE INVENTION

It was therefore an object of the invention to provide a process for preparing isocyanatoorganosilanes, in particular isocyanatomethylsilanes, having a significantly improved storage stability. These and other objects are achieved by purifying the isocyanatoorganosilanes and packaging and handling in an atmosphere containing less than 10% humidity.

DETAILED DESCRIPTION OF THE PREFERRED EMBODIMENTS

The invention thus provides a process for preparing silanes which have an isocyanate function, in which the silanes are purified after their chemical preparation and after purification are handled exclusively in an atmosphere having a relative atmospheric humidity of less than 10%.

The handling of the isocyanato-functional silanes comprises, inter alia, storage and also dispensing and/or transfer into containers suitable for storage and/or transport.

The process of the invention is preferably used for preparing isocyanato-functional silanes of the general formula (3)

$$OCN-(CH_2)_x-SiR^1_a(OR^2)_{3-a} \quad (3),$$

where
$R^1$ is an unsubstituted or halogen-substituted alkyl, cycloalkyl, alkenyl or aryl radical having from 1 to 10 carbon atoms,
$R^2$ is an alkyl radical which has from 1-20 carbon atoms and may be interrupted by nonadjacent —O— groups,
x is 1-8 and
a is 0, 1, 2 or 3.

As radicals $R^1$, preference is given to methyl, ethyl or phenyl groups. The radicals $R^2$ are preferably methyl or ethyl groups. The variable x is preferably 1 or 3, with a value of 1, i.e. the use of α-isocyanatomethylsilanes, being particularly preferred. a is preferably 0, 1 or 2, more preferably 0 or 1.

The chemical preparation of the isocyanato-functional silanes can be carried out by any process and is preferably carried out by a process described in the cited prior art, with thermal processes as described in U.S. Pat. No. 6,008,396, EP 0 212 058, EP 1 010 704, EP 0 649 850 or EP 1 343 793 or else the microwave processes described in WO 2005/056564 and WO 2005/055974 being particularly preferred.

The purification of the isocyanato-functional silanes is preferably carried out by means of one or more distillation steps. In the distillation, the silane is preferably vaporized by means of a thin film evaporator, a distillation pot or by feeding into a distillation column.

In the purification of the isocyanato-functional silanes, the last purification step preferably takes place in an atmosphere having a relative atmospheric humidity of less than 10%. Particular preference is given to all purification steps taking place in an atmosphere having a relative atmospheric humidity of less than 10%. In a purification by distillation, the last distillation step preferably takes place in an atmosphere having a relative atmospheric humidity of less than 10% or under reduced pressure, i.e. at a pressure of <100 mbar, preferably <10 mbar and more preferably <2 mbar. Particular preference is given to all distillation steps in a purification by distillation taking place in an atmosphere having a relative atmospheric humidity of less than 10% or else under reduced pressure, i.e. at a pressure of <100 mbar, preferably <10 mbar and more preferably <2 mbar.

The isocyanato-functional silanes after the purification are preferably handled, stored and/or dispensed or transferred into containers suitable for storage and/or transport exclusively in an atmosphere having a relative atmospheric humidity of less than 5% and more preferably exclusively in an atmosphere having a relative atmospheric humidity of less than 1%. These containers are preferably pretreated to remove any traces of water present from the interior of the container before filling. Suitable pretreatment methods are, for example, evacuation of the containers and subsequent flushing with the above-described gases or flushing with inert gas for a defined time using specific apparatuses which ensure optimal displacement of the gas originally present (siphon technology), displacement of the gas by heating the container, etc. These processes can be carried out at any temperatures and pressures of the gas. The gases used are dried and heated by methods according to the prior art, e.g. steam heat exchangers, electric heating, etc.

The atmosphere having an atmospheric humidity of less than 10% is preferably a protective gas atmosphere having a water content of less than 1000 ppm, with a water content of less than 500 ppm and in particular a water content of less than 250 ppm being particularly preferred. As protected gas, particular preference is given to using dried air, nitrogen or noble gases, with nitrogen or argon being particularly preferred.

The dispensing of the isocyanato-functional silanes, preferably the isocyanatosilanes corresponding to the general formula (3), where x is most preferably 1, into containers which are suitable for storage and/or transport and may have been pretreated is preferably carried out in a glove box in which the respective protective gas atmosphere is present. In an industrial process, dispensing in a hermetically sealed dispensing system, e.g. with dispensing valves provided with dead-space reconnections, is particularly preferred.

The invention is based on the surprising fact that the isocyanato-functional silanes, in particular the α-isocyanatomethylsilanes of the general formula (3) where x=1, have a significantly improved storage stability when they have never come into contact with (atmospheric) moisture after the last purification step.

Here, the group of α-isocyanatomethylsilanes of the general formula (3) where x=1 differs from all other isocyanates. Although all these latter compounds are able to react with atmospheric moisture, which is why these too cannot be stored in air over prolonged periods of time, conventional isocyanates require quantitative amounts of water (one molecule of water "destroyed" per each two molecules of isocyanate) and neither the water itself nor the decomposition products of the reaction of isocyanates with water possess catalytic activity. The decomposition of the isocyanate therefore stops as soon as contact with atmospheric moisture ceases.

For this reason, brief contact with air, for example during transfer or dispensing processes, is largely unproblematical in the case of conventional isocyanates since decomposition of the product occurs at best in the tiniest amounts and generally in undetectable trace amounts. Handling exclusively under protective gas is therefore neither necessary nor customary.

In contrast, in the case of the α-isocyanatomethylsilanes it has surprisingly been found that these are decomposed at an appreciably high rate even in the absence of atmospheric moisture as soon as they have come into contact even only once with atmospheric moisture during their "product history" without subsequently having been immediately purified again. That is to say, these compounds are, unlike all other isocyanates, extremely sensitive to even short contacts with air as occur during dispensing or transfer processes. Their otherwise greatly restricted storage capability can therefore be clearly increased when they are handled exclusively under protective gas or atmospheres which are low in water.

All symbols in the above formulae in each case have their meanings independently of one another.

EXAMPLES

In the following examples and comparative examples, all ground glass joints are greased with vacuum grease so that virtually perfect airtightness is ensured. Furthermore, all amounts and percentages are by weight, unless indicated otherwise. All reactions were carried out at a pressure of 0.10 MPa (abs.) and a temperature of 20° C.

α-isocyanatomethylmethyldimethoxysilane is prepared from α-methylcarbamatomethylmethyldimethoxysilane by the process described in EP 1 343 793. A crude product (R) having a content of α-isocyanatomethyldimethoxymethylsilane of about 91% is obtained.

Example 1

A conventional distillation apparatus having a distillation flask having a volume of 1 l, a packed column having a length of 30 cm and a standard Liebig condenser is used. The Liebig condenser has, as usual, a connection for attaching tubing at the end of the condenser section. As receiver for collecting the distillate, use is made of four 100 ml flasks which are connected via a distributor to the Liebig condenser and can thus be filled in succession by rotating the distributor without interrupting the distillation. Three of the four 100 ml receiver flasks are each additionally equipped with a connection with stopcock, but these remain closed during the entire distillation operation.

The apparatus is connected via the connection of the Liebig condenser by means of gastight vacuum tubing to a conventional laboratory protective gas facility in which the connected apparatus can be connected via a stopcock to either of two glass trains. The first glass train is evacuated by means of an oil pump, while argon at atmospheric pressure is passed through the second train.

Initially, the as yet unfilled distillation apparatus is evacuated via the laboratory protective gas facility (pressure<1 mbar) and carefully baked by means of a hot air blower (150° C.). The apparatus is subsequently flooded with argon. This operation is repeated a total of three times.

The still pot is subsequently charged with about 600 ml of the crude product (R) in a countercurrent of argon. The actual distillation is carried out at 30 mbar, a temperature at the bottom of 85-90° C. and a temperature at the top of about 82° C. A first fraction of about 50 ml is firstly distilled off and this is collected in the receiver flask without a connection with stopcock. The remaining three receiver flasks are then filled in succession with in each case about 60 ml. The distillation is subsequently stopped and the distillation apparatus is flooded with argon.

The three receiver flasks containing the main fractions are then connected via their connections to the laboratory protective gas facility, likewise by means of vacuum tubing. However, the stopcocks of the connections initially remain closed until the connecting tubing has in each case been evacuated three times via the protective gas facility each time flooded with argon. Only then are the three receiver flasks connected to the argon train by opening of the connection stopcocks, detached from the distillation apparatus in a countercurrent of argon and closed in an airtight manner with glass stoppers. The stopcocks of the connections are subsequently also closed again. The entire operation is repeated a second time, so that a total of six freshly distilled isocyanatosilane samples present under argon and sealed in an airtight manner are available.

Example 2

The procedure of example 1 is repeated, except that nitrogen instead of argon is used as protective gas. Here too, the entire distillation operation is repeated twice, so that a total of six freshly distilled isocyanatosilane samples present under nitrogen and sealed in an airtight manner are available.

These six samples are subsequently introduced into a nitrogen-filled glove box (moisture content<0.1% by weight) and there each transferred into another 100 ml flask which is then once again closed in an airtight manner by means of a glass stopper.

Comparative Example 1

The procedure of example 1 is repeated, except that normal air in the room (about 20° C., relative atmospheric humidity about 50%) is used instead of protective gas for breaking the vacuum of the distillation apparatus. In addition, the main fraction flasks after conclusion of the distillation are removed without any particular precautions from the distillation apparatus and subsequently closed in an airtight manner.

Here too, the entire distillation operation is repeated twice, so that a total of six freshly distilled isocyanatosilane samples sealed in an airtight manner are available.

Comparative Example 2

The procedure of comparative example 1 is repeated exactly. However, the six freshly distilled samples are transferred in air (about 20° C., relative atmospheric humidity about 50%) into another 100 ml flask which is subsequently once again closed in an airtight manner.

Example 3

In each case five of the samples produced in all examples and comparative examples are stored in their airtight containers for 3, 6, 9, 12 and 15 weeks at about 20° C. Their NCO content is subsequently determined. One sample from each of the examples and comparative examples is analyzed immediately after having been prepared. All samples are discarded after analysis, i.e. a fresh sample which has not yet been opened after having been prepared is analyzed at each of the six measurement times.

The determination of the NCO content is carried out by means of wet chemical analysis. Here, a known amount of the sample substance is reacted with an excess of dibutylamine to form the corresponding N-(methyldimethoxysilylmethyl)-N',N'-dibutylurea and the unconsumed amine is titrated by means of hydrochloric acid. The content of isocyanate groups in the sample is calculated from the difference between HCl consumed and amine used [theoretical value for a purity of 100%: 26.1%.]

The following table shows the purities calculated from the respective NCO contents for the samples from the examples and comparative examples after the storage time indicated in each case. As can be seen from the values for a storage time of <1 day, the value for the freshly distilled samples is over 97% for all examples and comparative examples. That is to say, the brief contact with atmospheric moisture of the samples from the comparative examples has not led to any significant immediate product decomposition.

| Storage time | Sample from ex. 1 | Sample from ex. 2 | Sample from c. ex. 1 | Sample from c. ex. 2 |
| --- | --- | --- | --- | --- |
| <1 Day | 97.7% | 98.0% | 97.8% | 97.1% |
| 3 Weeks | 97.0% | 97.4% | 96.0% | 95.4% |
| 6 Weeks | 96.5% | 97.0% | 94.2% | 92.6% |
| 9 Weeks | 95.0% | 95.1% | 93.1% | 90.1% |
| 12 Weeks | 94.4% | 94.6% | 91.5% | 88.6% |
| 15 Weeks | 93.1% | 93.0% | 87.2% | 83.2% |

It can be seen that the samples treated according to the invention from examples 1 and 2 have a significantly greater storage stability than the samples from the comparative examples.

The invention claimed is:

1. A process for preparing silanes containing an isocyanate group, wherein the silanes are purified after their chemical preparation, and directly after purification by one or more purification steps are handled exclusively in an atmosphere having a relative atmospheric humidity of less than 10%.

2. The process of claim 1, wherein the isocyanate-functional silanes containing an isocyanate group have the formula (3)

OCN—(CH$_2$)$_x$—SiR$^1_a$(OR$^2$)$_{3-a}$      (3), where

R$^1$ is an unsubstituted or halogen-substituted alkyl, cycloalkyl, alkenyl or aryl radical having from 1 to 10 carbon atoms, R$^2$ is an alkyl radical which has from 1-20 carbon atoms and may be interrupted by nonadjacent —O— groups, x is 1-8 and a is 0, 1, 2 or 3.

3. The process of claim 2, wherein x is 1.

4. The process of claim 1, wherein the purification of the silanes containing an isocyanate group is carried out by means of one or more distillation steps.

5. The process of claim 1, wherein a last purification step in the purification of the silanes containing an isocyanate group takes place in an atmosphere having a relative atmospheric humidity of less than 10%.

6. The process of claim 1, wherein the atmosphere is a protective gas atmosphere and the protective gas is selected from among dried air, nitrogen and noble gases.

7. The process of claim 1, wherein the water content of gas present in a purificative distillation or which contacts the purified silanes containing an isocyanate group after purification has a water content of less than 1000 ppm.

8. The process of claim 1, wherein following purification, gas contacting the purified silanes containing an isocyanate group prior to storage in a storage container has less than 5% atmospheric humidity.

9. The process of claim 1, wherein following purification, gas contacting the purified silanes containing an isocyanate group prior to storage in a storage container has less than 1% atmospheric humidity.

10. The process of claim 1, wherein purified silanes containing an isocyanate group is introduced into a storage container which has been freed of moisture by one or more of heating, evacuation, or flushing with dried gas.

11. The process of claim 1, wherein one or more distillations are used to purify the silanes containing an isocyanate group, and at least a last distillation, when two or more distillations are used, and the sole distillation, when one distillation is used, is conducted in an atmosphere containing less than 5% relative humidity.

12. The process of claim 11, wherein air with a water content of less than 1000 ppm is used in the distillation.

13. The process of claim 11, wherein dry nitrogen or inert gas is used in the distillation.

* * * * *